United States Patent
Rego et al.

(10) Patent No.: US 10,937,553 B2
(45) Date of Patent: Mar. 2, 2021

(54) SYSTEMS AND METHODS TO ORGANIZE THE FLOW AND PROCESSING OF QUEUED MESSAGES THAT HAVE BEEN RECEIVED FROM HEALTHCARE ENTITIES

(71) Applicant: Redox, Inc., Madison, WI (US)

(72) Inventors: Blake Rego, North Bay Village, FL (US); Brandon Palmer, Madison, WI (US); Tanner Engbretson, Madison, WI (US)

(73) Assignee: Redox, Inc., Madison, WI (US)

( * ) Notice: Subject to any disclaimer, the term of this patent is extended or adjusted under 35 U.S.C. 154(b) by 338 days.

(21) Appl. No.: 16/189,609

(22) Filed: Nov. 13, 2018

(65) Prior Publication Data

US 2020/0152337 A1 May 14, 2020

(51) Int. Cl.
*G16H 80/00* (2018.01)
*H04L 12/58* (2006.01)
*G06F 9/54* (2006.01)

(52) U.S. Cl.
CPC ............ *G16H 80/00* (2018.01); *G06F 9/546* (2013.01); *H04L 51/22* (2013.01); *H04L 51/26* (2013.01)

(58) Field of Classification Search
CPC ........ G16H 80/00; G16H 40/60; G16H 10/60; H04L 51/26; H04L 51/066; H04L 51/22; G06F 9/546; G06F 9/488
See application file for complete search history.

(56) References Cited

U.S. PATENT DOCUMENTS

| | | | |
|---|---|---|---|
| 5,546,580 A * | 8/1996 | Seliger | G16H 40/67 |
| 7,752,035 B2 | 7/2010 | Oon | |
| 8,000,984 B2 | 8/2011 | Hasan | |
| 8,260,635 B2 | 9/2012 | Hasan | |
| 8,756,613 B2 * | 6/2014 | Hosie | G06F 9/546 |
| | | | 719/314 |
| 8,850,057 B2 | 9/2014 | Natoli | |
| 9,137,166 B2 * | 9/2015 | Lee | H04L 47/34 |
| 2001/0053986 A1 | 12/2001 | Dick | |
| 2004/0068545 A1 | 4/2004 | Daniell | |
| 2005/0138210 A1 | 6/2005 | Shkvarchuk | |
| 2007/0016450 A1 | 1/2007 | Bhora | |
| 2008/0046292 A1 | 2/2008 | Myers | |
| 2008/0148282 A1 * | 6/2008 | Sodani | G06F 9/3865 |
| | | | 719/314 |
| 2009/0222283 A1 | 9/2009 | Lassetter | |

(Continued)

Primary Examiner — Oanh Duong
(74) Attorney, Agent, or Firm — Esplin & Associates, PC

(57) ABSTRACT

Systems and methods to organize the flow and processing of queued messages may: receive messages in a set of processing queues; select a first and second processing queue; select a first and second message in the first and second processing queue; process the concurrent portions of the first and second message simultaneously; select a third processing queue and determine a subset of messages that are its oldest messages; assign a first sequential numbering to the messages in the subset; assign a second sequential numbering to those messages in the subset having a concurrent portion that has been previously processed and a sequential portion that has not been previously processed; determine whether the oldest message in the subset was assigned the same number in the first sequential numbering and the second sequential numbering, and, if so, process the sequential portion of the oldest message.

20 Claims, 4 Drawing Sheets

(56) References Cited

U.S. PATENT DOCUMENTS

2010/0169263 A1 7/2010 Korpman
2011/0106564 A1 5/2011 Hachmeister
2015/0332011 A1 11/2015 Ting
2016/0063191 A1 3/2016 Vesto
2019/0221296 A1 7/2019 Lloyd

* cited by examiner

SYSTEMS AND METHODS TO ORGANIZE THE FLOW AND PROCESSING OF QUEUED MESSAGES THAT HAVE BEEN RECEIVED FROM HEALTHCARE ENTITIES

FIELD OF THE DISCLOSURE

The present disclosure relates to systems and methods to organize the flow and processing of queued messages, wherein the messages are received from healthcare entities. Individual messages may be processed by converting and/or transforming some or all of the contents and/or formatting.

BACKGROUND

Exchanging messages, including but not limited to medical records, medical activity and/or other transactional information, between different healthcare entities is known. Exchanging messages between healthcare entities and vendor entities (by way of non-limiting example, insurance companies, pharmacies, etc.) is known. Healthcare entities and third party vendors often communicate in order to carry out and/or facilitate various healthcare related services. Processing messages by converting and/or transforming some or all of the contents and/or formatting is known and could, e.g., be performed by the health care entities or by the vendor entities.

SUMMARY

One aspect of the present disclosure relates to a system configured to organize the flow and processing of queued messages. Individual messages may be received from healthcare entities and may be intended for vendor entities. The system may operate as an intermediary between healthcare entities and vendor entities. The system may include one or more hardware processors configured by machine-readable instructions. As used herein, the term "hardware processor" may be used interchangeably with the term "processor." The processor(s) may be configured to receive, from one or more healthcare entities, messages in a set of processing queues. A processing queue may be configured to receive messages, e.g., from one or more healthcare entities. In some implementations, and/or in some aspects, processing queues may operate as first-in-first-out queues, or FIFOs. In some implementations, processing queues may be configured to process at least a portion of messages. Alternatively, and/or simultaneously, in some implementations, processing engines may be configured to process at least a portion of messages. As used herein, the processing of messages may refer to one or more of analyzing the contents and/or formatting of messages, transforming the contents and/or formatting of messages, converting the contents and/or formatting of messages, extracting information from messages, and/or other automated operations performed on messages. Subsequent to being processed, the messages are transmitted to vendor entities.

The set of processing queues may include more than two processing queues. Individual messages may be received in individual processing queues. For example, in some implementations, a particular message may be received in only one processing queue. The individual messages may include a timestamp reflecting a time of receipt, the individual messages further including a concurrent portion and/or a sequential portion. The processor(s) may be configured to select a first processing queue from the set of processing queues based on the first processing queue including at least one message having a concurrent portion and a sequential portion that have not been previously processed, e.g., by the set of processing queues and/or the set of processing engines. The processor(s) may be configured to select a first individual message in the first processing queue. The processor(s) may be configured to select a second processing queue from the set of processing queues based on the second processing queue including at least one message having a concurrent portion and a sequential portion that have not been previously processed, e.g., by the set of processing queues and/or the set of processing engines. The processor(s) may be configured to select a second individual message in the second processing queue. The processor(s) (and/or one or more other components of the system) may be configured to process the concurrent portions of the first individual message, the second individual message, and/or other messages simultaneously. As used herein, processing messages or portions of messages simultaneously means that at least some part of the duration of processing overlaps among the multiple messages or portions of messages. The processor(s) may be configured to select a third processing queue from the set of processing queues based on the third selected processing queue including at least one message having a concurrent portion that has been previously processed and a sequential portion that has not been previously processed. The processor(s) may be configured to determine a subset of messages in the third processing queue based on the messages in the subset being the oldest messages in the third processing queue. The determination of being the oldest messages may be based on the timestamps reflecting the times of receipt of the messages in the third subset. The processor(s) may be configured to assign a first sequential numbering to the messages in the subset. The processor(s) may be configured to assign a second sequential numbering to those messages in the subset that have a concurrent portion that has been previously processed and a sequential portion that has not been previously processed. The processor(s) may be configured to determine an oldest message in the subset. The determination may be based on the timestamps reflecting the times of receipt for the messages in the subset. The processor(s) may be configured to determine whether the oldest message was assigned the same number in the first sequential numbering and the second sequential numbering. The processor(s) may be configured to, responsive to the determination being positive and/or affirmative, process the sequential portion of the oldest message. The processor(s) may be configured to remove the oldest message from the set of processing queues and/or transmit the oldest message to an appropriate vendor entity.

Another aspect of the present disclosure relates to a method to organize the flow and processing of queued messages. Individual messages may be received from healthcare entities and may be intended for vendor entities. The method may include receiving, from one or more healthcare entities, messages in a set of processing queues. The set of processing queues may include more than two processing queues. Individual messages may be received in individual processing queues. The individual messages may include a timestamp reflecting a time of receipt, the individual messages further including a concurrent portion and/or a sequential portion. The method may include selecting a first processing queue from the set of processing queues based on the first processing queue including at least one message having a concurrent portion and a sequential portion that have not been previously processed, e.g., by the set of processing queues. The method may include selecting a first individual message in the first processing queue. The method may include selecting a second processing queue from the set of processing queues based on the second processing queue including at least one message having a concurrent portion and a sequential portion that have not been previously processed, e.g., by the set of processing queues. The method may include selecting a second individual message in the second processing queue. The method may include processing the concurrent portions of both the first individual message and the second individual message simultaneously. The method may include selecting a third processing queue from the set of processing queues based on the third selected processing queue including at least one message having a concurrent portion that has been previously processed and a sequential portion that has not been previously processed. The method may include determining a subset of messages in the third processing queue based on the messages in the subset being the oldest messages in the third processing queue. The determination of being the oldest messages may be based on the timestamps reflecting the times of receipt of the messages in the third subset. The method may include assigning a first sequential numbering to the messages in the subset. The method may include assigning a second sequential numbering to the messages in the subset having a concurrent portion that has been previously processed and a sequential portion that has not been previously processed. The method may include determining an oldest message in the subset based on the timestamps reflecting the times of receipt for the messages in the subset. The method may include determining whether the oldest message was assigned the same number in the first sequential numbering and the second sequential numbering. The method may include, responsive to a positive and/or affirmative determination, processing the sequential portion of the oldest message. The method may include removing the oldest message from the set of processing queues.

As used herein, any association (or relation, or reflection, or indication, or correspondency) involving users, client computing platforms, processors, messages, queues, healthcare entities, portions of messages, sets of messages, timestamps, numberings, subjects, patients, assets, conversions, transformations, and/or another activity, entity, and/or object that interacts with any part of the system and/or plays a part in the operation of the system, may be a one-to-one association, a one-to-many association, a many-to-one association, and/or a many-to-many association or N-to-M association (note that N and M may be different numbers greater than 1).

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 4A-4B-4C-4D illustrate exemplary states of (sets of) processing queues as may be used by a system to organize the flow and processing of queued messages, in accordance with one or more implementations.

DETAILED DESCRIPTION

Figure 1:
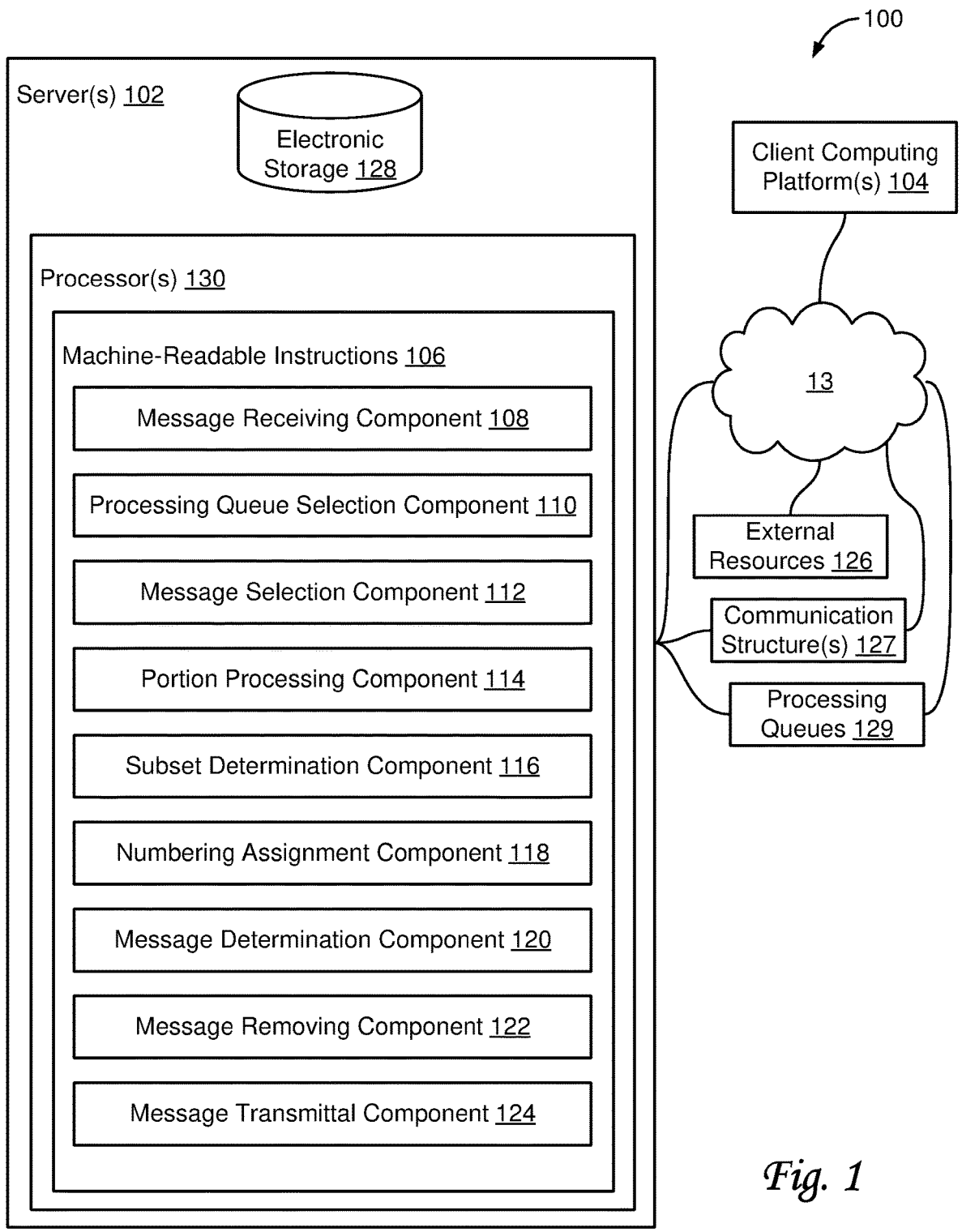
FIG. 1 shows a system configured to organize the flow and processing of queued messages, wherein the messages are received from healthcare entities, in accordance with one or more implementations.

FIG. 1 illustrates a system 100 configured to organize the flow and processing of queued messages. The messages may be received from healthcare entities. The messages may be intended for vendor entities. In some implementations, system 100 may include one or more servers 102, processing queues 129, communication structures 127, external resources 126, and/or other components. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104. Communication may include a network 13, such as the Internet and/or other networks.

In some implementations, healthcare entities may include entities that provide and/or facilitate healthcare related services. Healthcare entities may include one or more of medical offices, hospitals, medical labs, public healthcare agencies, and/or other entities.

Third parties may interact with healthcare entities. The third parties may include vendors who provide services that may be supplemental to and/or additional to services provided by the healthcare entities. A vendor may be referred to as a "vendor entity." A vendor entity may include one or more of an insurance company, a pharmacy, and/or other service providers that may communicate and/or interact with healthcare entities.

In some implementations, healthcare entities may exchange information (e.g., transactional information in the form of messages) with vendor entities in order to facilitate the services provided by either, or both, parties. The exchange may be provided via a real-time, publish-subscribe architecture. By way of non-limiting illustration, messages related to patient scheduling may be communicated when an appointment is scheduled, cancelled, and/or modified. With this type of exchange of information, it may be up to the receiving third parties to identify the relevant information from these messages in order to reconstruct the content of the message in a way that is usable to them. This can often be difficult and/or error-prone. Accordingly, the systems and methods presented operate on healthcare information (e.g., transactional information and/or other information) exchanged between parties. This may take the burden of identifying and/or reconstructing the relevant information off the third party vendor entities. Instead, the vendor entities may simply receive messages in a format usable to them.

Server(s) 102 may be configured by machine-readable instructions 106. Machine-readable instructions 106 may include one or more instruction components. The instruction components may include computer program components. The instruction components may include one or more of a message receiving component 108, a processing queue selection component 110, a message selection component 112, a portion processing component 114, a subset determination component 116, a numbering assignment component 118, a message determination component 120, a message removing component 122, a message transmittal component 124, and/or other instruction components.

Figure 3:
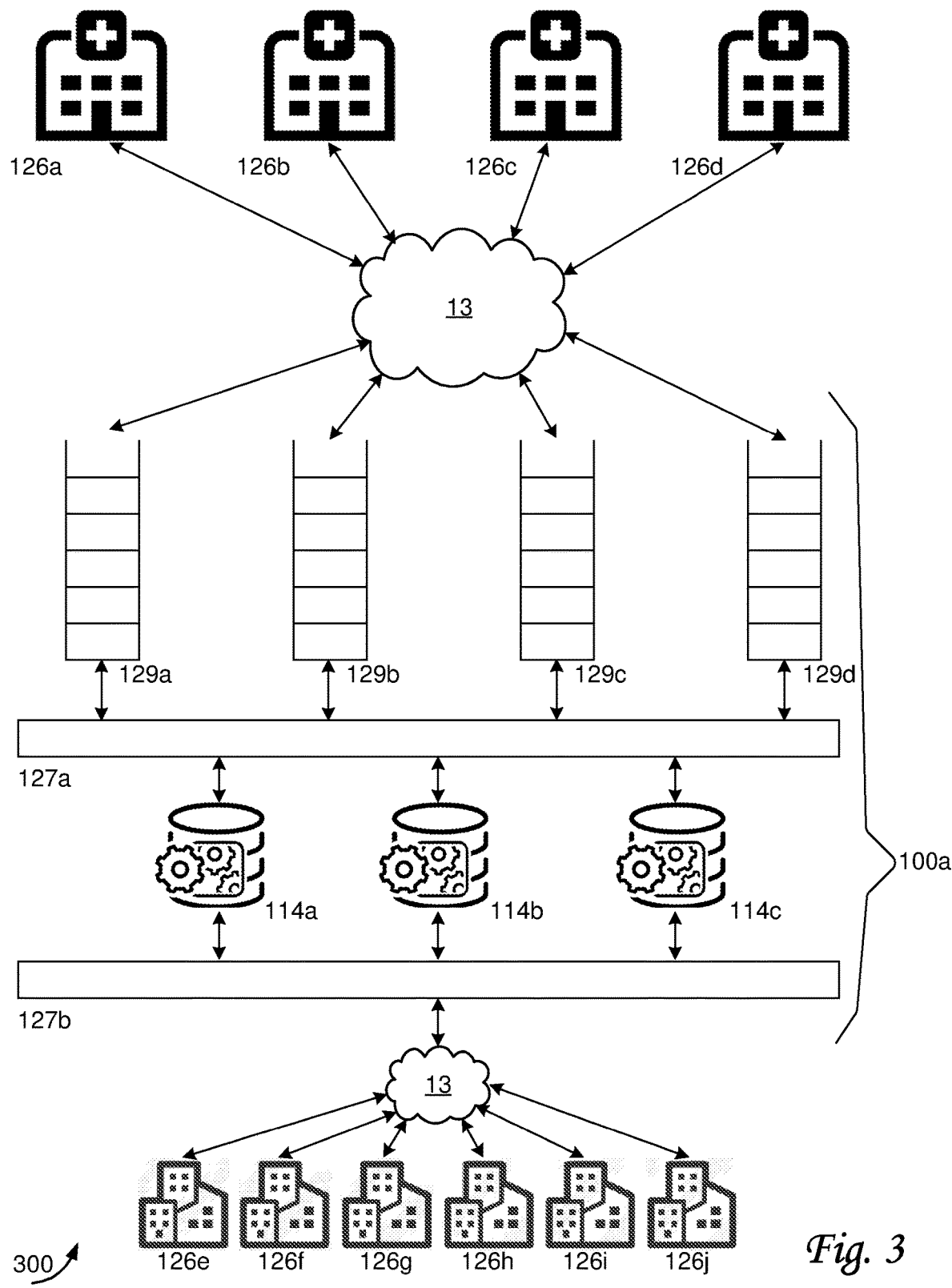
FIG. 3 illustrates components of a system to organize the flow and processing of queued messages, in accordance with one or more implementations.

By way of non-limiting example, FIG. 3 illustrates an example 300 of how various components of a system 100a (which may be a version, variation, or instance of system 100 as shown in FIG. 1) may interact to organize the flow and processing of queued messages. Healthcare entities such as hospitals may be regarded as part of external resources 126 (shown in FIG. 1). In particular a first, second, third, and fourth hospital may be indicated in FIG. 3 as external resource 126a, 126b, 126c, and 126d, respectively. The individual hospitals may send messages via a network 13 to system 100a that are received by a processing queue 129a, 129b, 129c, and 129d (these may be instances of processing queues 129 as shown in FIG. 1). The messages may be routed to different components for processing via a first communication structure 127a (this may be an instances of communication structure 127 as shown in FIG. 1). The different components for processing may include a first processing engine 114a, a second processing engine 114b, and a third processing engine 114c (these may be versions, variations, or instances of portion processing component 114 as shown in FIG. 1). Once a message has been (completely) processed, a second communication structure 127b may be used to route the message, e.g., via a network similar or the same as network 13, to one of vendor entities 126e, 126f, 126g, 126h, 126i, or 126j. Vendor entities such as insurance companies may be regarded as part of external resources 126 (shown in FIG. 1).

Referring to FIG. 1, message receiving component 108 may be configured to receive messages. In some implementations, message receiving component 108 may be configured to receive, from one or more healthcare entities, messages in a set of processing queues. The set of processing queues may include more than two processing queues. Individual messages may be received in individual processing queues. For example, in some implementations, each message may only be received in one processing queue. The individual messages may represent events involving subjects and assets of the individual health care entities. The individual messages each may have a format that is specific to one or more of the individual health care entities.

In some implementations, messages may include healthcare information. The healthcare information may include information derived from transactional information and/or other information. The transactional information may include information exchanged between different parties within a given healthcare entity, between multiple healthcare entities, between a healthcare entity and a third party, between a healthcare entity and multiple third parties, between a healthcare entity and a vendor entity, and/or other information. In some implementations, message content of the messages may include, involve, and/or refer to other healthcare information (e.g., patient identification information, electronic health records, and/or other information). The message content of an individual message may define one or more events. An event may include a transaction or exchange that describes a subject's involvement with one or more healthcare entities for the purpose of treating the subject. The involvement may include one or more of past, present, and/or future involvement. More specifically, an event may involve an individual subject being treated and one or more assets of one or more healthcare entities that may be utilized during the treatment. The transactional information may be analyzed to ascertain the events described therein, the subjects involved, the assets involved, and/or other information. The status of these events, subjects, and/or assets may comprise the information which is received.

The healthcare information may include one or more of electronic health records, information records derived from transactional information, and/or other information. Electronic health records may include one or more of patient identification information, patient health information, and/or other information. The patient identification information may include information used to identify individual subjects. The patient identification information may include one or more of patient identifiers, patient name, gender of a patient, and/or other information. The patient health information may include one or more of administrative and/or billing information, patient demographics, progress notes, vital signs, medical histories, diagnoses, medications, immunization dates, allergies, radiology images, lab and test results, and/or other information.

Transactional information may include information exchanged between parties within a healthcare entity, between multiple healthcare entities, between a healthcare entity and a third party, and/or other information. The information may be exchanged between parties and/or entities via messages. The messages may include message content which includes the transactional information. In some implementations, the message content may include, involve, and/or refer to other healthcare information (e.g., patient identification information, electronic health records, and/or other information). By way of non-limiting example, message content of an individual message may define one or more events. An event may include a transaction or exchange that describes a subject's involvement with one or more healthcare entities for the purpose of treating the subject. The involvement may include one or more of past, present, and/or future involvement. More specifically, an event may involve an individual subject being treated and one or more assets of one or more healthcare entities that may be utilized during the treatment. The transactional information may be analyzed to ascertain the events described therein, the subjects involved, the assets involved, and/or other information. These events, subjects, and/or assets may be described in information records which may be stored and/or made searchable.

An asset of a healthcare entity may describe an offering that a healthcare provides to its' patients. An asset may include one or more of services provided to patients, resources utilized by patients, and/or other assets. An asset may be classified by type. The asset types may be further classified by sub-type. The asset types may include one or more of a resource type, a services type, and/or other types.

A resource type asset may include physical resources available within a healthcare facility and/or other assets. For example, resource type assets may include one or more of personnel that interact with patients (e.g., doctors, nurses, specialists, etc.), equipment used to treat patients (e.g., CT scanner, respirator, etc.), depletable resources used during patient treatment (e.g., drugs, food, etc.), facilities in which treatment takes place (e.g., recovery room, emergency room, operating room, etc.), and/or other assets. The resource type assets may be further classified by subtype. The subtypes may include one or more of personnel subtype, equipment subtype, depletable resource subtype, facility subtype, and/or other subtypes. For example, doctors, nurses, specialists, and/or other personnel may be categorized as a resource type asset of the personnel subtype. A CT scanner, respirator, and/or other equipment may be categorized as a resource type asset of the equipment subtype. Drugs, food, and/or other depletable resources may be categorized as a resource type asset of the depletable resource subtype. A recovery room, emergency room, an operating room, and/or other facilities may be categorized as a resource type asset of the facility subtype.

A services type asset may include intangible services available within a healthcare facility and/or other assets. For example, a services type asset may include one or more of a scheduling service, a drug prescription service, and/or other services. The services type assets may be further classified by subtype. The subtypes may include one or more of a scheduling subtype, a prescription subtype, and/or other subtypes. For example, a scheduling service may be categorized as a services type asset of the scheduling subtype. A drug prescription service may be categorized as a services type asset of the prescription subtype.

In some implementations, a services type asset may specify one or more resource type assets involved in a service. For example, scheduling a patient for surgery may specify one or more of a particular surgeon (a resource type asset of the personnel subtype), a particular operating room (a resource type asset of the facility subtype), a time, a date, and/or other information. Further, assigning a prescription to a patient may specify the prescribing doctor (a resource type asset of the personnel subtype), the drug being prescribed (a resource type asset of the depletable resource subtype), and/or other information.

In some implementations, message content may be represented in a variety of formats (e.g., medical record formats). Healthcare entities may utilize their own custom format. By way of non-limiting example, customizations may be directed one or both of the representation of message content in individual messages and/or the location of message content in individual messages. A transformation may be applied to the message content to transform the message content to a healthcare entity-independent format. The transformation may be applied prior to ascertaining the events described in the messages, the subjects involved in the events, and/or the assets involved in the events. The healthcare entity-independent format may represent the message content in a standardized, consistent, manner. The message content in the healthcare entity-independent format may be found in the same place regardless of the source of the information (e.g., regardless of the healthcare entity customizations), making ascertaining the information included therein more streamline.

The healthcare entities may store and/or communicate healthcare information. The healthcare information may be stored and/or communicated in different formats (e.g., medical record formats) for different healthcare entities. Individual healthcare entities may be associated with different medical record formats such that an individual healthcare entity may store and/or communicate information in a format associated with that individual healthcare entity. As presented herein, medical record formats may be customized by the individual healthcare entities. The medical record formats may follow one or more standards used in the healthcare industry. The customizations may be independent of the standard utilized by a healthcare entity. The various standards may refer to a framework for the exchange, integration, sharing, and/or retrieval of information. For example, the standards may include one or more of Health Level 7 (HL7), EDIFACT, DICOM, X12N, NCPDP, and/or other standards. The standards may be based on past standards, current standards, and/or future standards. For example, HL7 may include different versions such as HL7v2, HL7v3, and/or other HL7 versions. Individual versions of HL7 may be associated with various countries. For example, the standards may include an Australian version of HL7v3, a United Kingdom version of HL7v3, a United States version of HL7v3, and/or other versions of HL7.

Customizations of the medical record formats may be directed the representation of information. Certain information may be represented differently within different custom medical record formats. By way of non-limiting example, "Female" may be represented as one or more of "F", "Female", "FEMALE", "W", "Woman", "WOMAN", as an integer (e.g., 1 or 2) that corresponds to a value for male or female, and/or may be represented in others ways within different medical record formats.

Customizations of the medical record formats may be directed the location of information in individual messages. For example, a message may include message content. For different medical record formats, a specific piece of information (e.g., gender of a patient, patient identifier, etc.) may reside in different locations within a message depending on the medical record format.

In some implementations, individual healthcare entities that may use the same or similar medical record format may have a specific set of variations in common across their customers. Further, individual healthcare entities may have unique variations within their own customizations. As such, simply because HL7 (or other standard) may be associated with and/or used by a first healthcare entity as a standard of practice, it does not necessarily mean that the medical record format of a second healthcare entity, which also uses HL7 (or other standard) in their practice, is the same format as the format used by the first healthcare entity. That is, individual healthcare entities that utilize HL7 (or other standard) as their standard in practice, may individually customize the medical record format that may still be within the guidelines of HL7 (or other standard).

Configuration records may be used to solve the problem of the variations in the locations and/or representations of information within medical record formats of different healthcare entities. For individual healthcare entities, individual configuration records may be stored. The configuration records may include sets of rules, which when applied to the activity of processing a message, may "normalize" or "standardize" the message content into a healthcare entity-independent format. For example, representations of information may be transformed into a common form of the information and/or locations of information may be transformed into common locations. The transformation may still maintain the information in accordance with the guidelines set by one or more standards. Returning to the example of a patient's gender above, "female" may be represented differently among different medical record formats. The configuration records may normalize or standardize such differences in representation. Further, where a specific piece of information (e.g., gender of a patient, patient identifier, etc.) may reside in different locations within the message depending on the medical record format, the configuration records may normalize or standardize such differences in locations to a common location within a "normalized" or "standardized" message.

In some implementations, configuration records (e.g., the set of rules) may use a domain specific language (DSL) to transform the message content of the messages to the healthcare entity-independent format.

The individual messages may include a timestamp reflecting a time of receipt, a concurrent portion, a sequential portion, and/or other portions or information. In some implementations, messages from a particular source (e.g., an individual external resource 126) need to be transmitted to their destination (e.g., a vendor entity) in the same sequence as they were sent. The portion of a message used to facilitate this sequence (and/or accomplish this sequence) is referred to as the sequential portion. The portion of a message that may be transformed, formatted, and/or is otherwise not part of the sequential portion is referred to as the concurrent portion. In some implementations, the sequential portion and the concurrent portion of a message may be mutually exclusive portions. The sequential portion of the individual messages may need to be processed after the concurrent portion of the individual messages. In some implementations, processing of the concurrent portion of the individual messages may be performed by one or more processing engines from a set of processing engines. In some implementations, processing of the concurrent portion of an individual message may include transforming one or more of contents and/or formatting of the concurrent portion of the individual message. Transforming the formatting of the concurrent portion of the individual message may cause the individual message to have a format that is common among two or more health care entities. A transformation may be tailored to a customization by an individual healthcare entity. Alternatively, and/or simultaneously, a transformation may target one or more standards used in the healthcare industry. In some implementations, a transformation may be tailored to one or more vendor entities. In some implementations, a transformation may use and/or result in a healthcare entity-independent format.

Processing queue selection component 110 may be configured to select one or more processing queues from the set of processing queues. In some implementations, processing queue selection component 110 may be configured to select a first processing queue from the set of processing queues. In some implementations, selection may be based on the first processing queue including at least one message having a concurrent portion and a sequential portion that have not been previously processed, e.g., by the set of processing queues. In some implementations, selection by processing queue selection component 110 may be based on a round-robin selection among the available and/or suitable processing queues. In some implementations, selection by processing queue selection component 110 may be performed randomly (e.g., stochastically and/or pseudo-stochastically) among the available and/or suitable processing queues.

Processing queue selection component 110 may be configured to select a second, third, fourth, processing queue from the set of processing queues, and so forth. In some implementations, selection may be based on the second processing queue including at least one message having a concurrent portion and a sequential portion that have not been previously processed, e.g., by the set of processing queues. In some implementations, processing queue selection component 110 may be configured to select as many processing queues from the set of processing queues as the number of messages (or concurrent portions of messages) system 100 can process simultaneously.

Figures 4A, 4B, 4C, 4D:
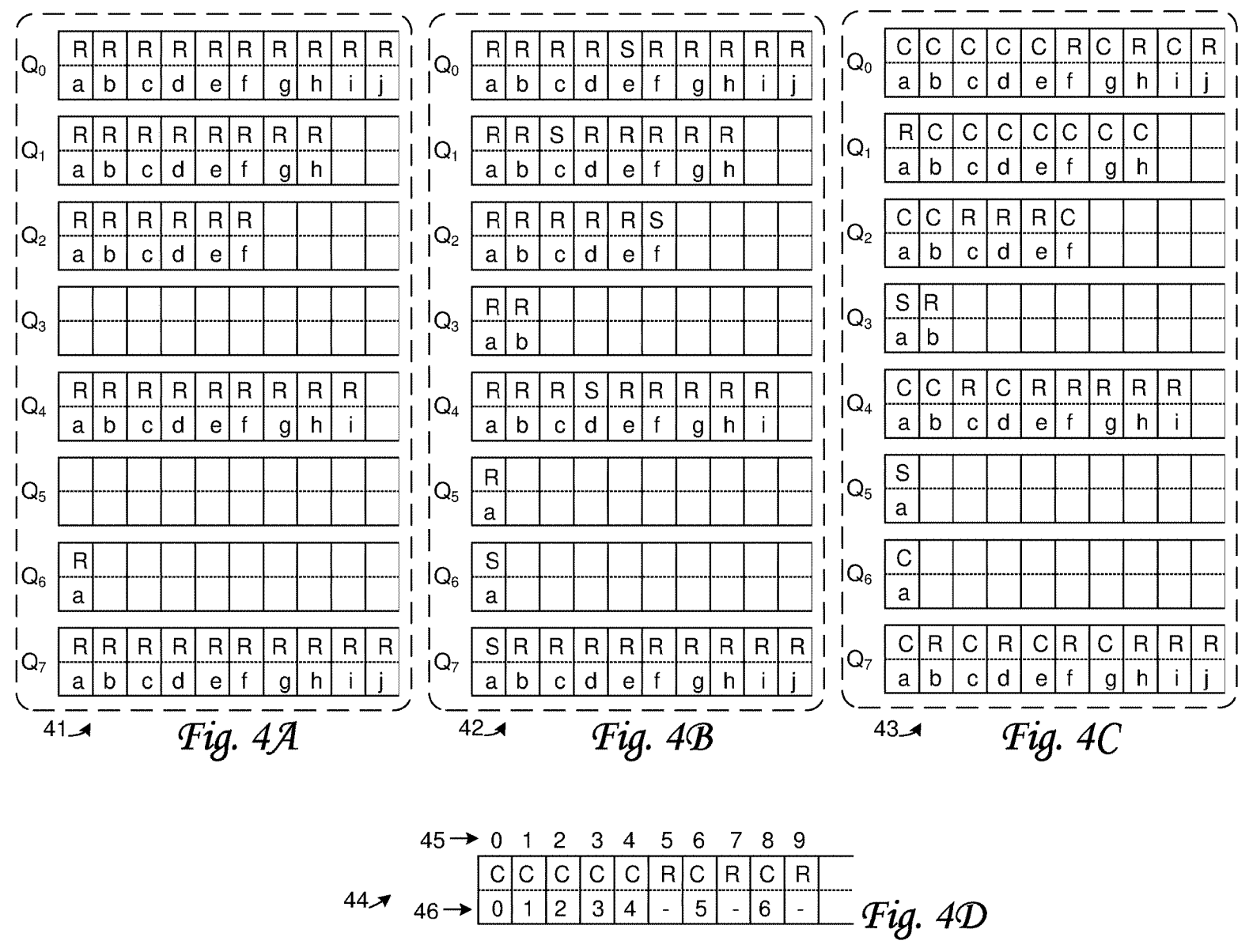

By way of non-limiting example, FIG. 4A illustrates (within a dashed line) an exemplary state 41 of a set of 8 processing queues as may be used by system 100. The set of processing queues includes a first processing queue labeled $Q_0$, a second processing queue labeled $Q_1$, and so forth until the eighth processing queue labeled $Q_7$. Each of the processing queues includes 10 slots that can be occupied by a message. The first slot, if used, is labeled "a," the second "b," and so forth until the tenth slot labeled "j". As shown in FIG. 4A, $Q_0$ includes 10 messages, $Q_1$ includes 8 messages, $Q_2$ includes 6 messages, $Q_3$ includes zero messages, $Q_4$ includes 9 messages, $Q_5$ includes zero messages, $Q_6$ includes 1 message, and $Q_7$ includes 10 messages. Above each label of a slot in a processing queue that is occupied by a particular message, exemplary state 41 includes the processing status of the particular message. The status "R" may indicate the message has not been previously processed (i.e., neither the concurrent portion nor the sequential portion has been processed by some component of system 100), and the concurrent portion of the particular message is ready for processing. Processing queue selection component 110 may select a first processing queue and/or a second processing queue from any of the processing queues that has at least one message with status "R", which is processing queues $Q_0$, $Q_1$, $Q_2$, $Q_4$, $Q_6$, and $Q_7$. Some mechanism may be implemented to assure no processing queue is starved by another processing queue. By way of non-limiting example, a round robin mechanism may cycle through all the available processing queues.

Message selection component 112 may be configured to select messages in particular processing queues. In some implementations, message selection component 112 may be configured to select a first individual message in the first processing queue (as selected by processing queue selection component 110). Selecting the first individual message in the first processing queue may include rendering the first individual message (temporarily) unavailable for selection by other processing engines in the set of processing engines. In some implementations, message selection component 112 may be configured to select a second individual message in the second processing queue (as selected by processing queue selection component 110). Likewise a third, fourth, fifth message in a third, fourth, fifth processing queue may be selected, and so forth. In some implementations, selection by message selection component 112 may be based on the timestamps of the available and/or suitable messages. In some implementations, selection by message selection component 112 may be based on a stochastically and/or pseudo-stochastically selecting from the available and/or suitable messages. In some implementations, selection by message selection component 112 may be based on a round-robin selection among the available and/or suitable messages. In some implementations, message selection component 112 may be configured to select as many messages as the number of messages (or concurrent portions of messages) system 100 can process simultaneously. In some implementations, some individual messages may not require any transformation or formatting, so that only the sequential portion needs to be processed.

By way of non-limiting example, FIG. 4B illustrates (within a dashed line) an exemplary state 42 of a set of 8 processing queues as may be used by system 100. Exemplary state 42 may be similar to exemplary state 41 of FIG. 4A, except that individual messages have been selected by message selection component 112 in processing queues $Q_0$, $Q_1$, $Q_2$, $Q_4$, $Q_6$, and $Q_7$. The selected slots are labeled "e", "c", "f", "d", "a", and "a", respectively.

Portion processing component 114 may be configured to process messages and/or portions of messages. In some implementations, portion processing component 114 may be configured to process the concurrent portions of multiple messages simultaneously. For example, portion processing component 114 may be configured to process the concurrent portions of both the first individual message (as selected, e.g., by message selection component 112) and the second individual message (as selected, e.g., by message selection component 112) simultaneously. As used herein, processing the concurrent portions of both the first individual message and the second individual message simultaneously may include processing at least a segment of the concurrent portion of the first individual message at the same time as processing at least a segment of the concurrent portion of the second individual message.

Processing queue selection component 110 may be configured to select a third processing queue from the set of processing queues. In some implementations, selection may be based on the third selected processing queue including at least one message having a concurrent portion that has been previously processed (e.g., by portion processing component 114) and a sequential portion that has not been previously processed. In some implementations, selection may be based on the third selected processing queue including at least one message having a concurrent portion that does not need to be processed and a sequential portion that has not been previously processed.

By way of non-limiting example, FIG. 4C illustrates (within a dashed line) an exemplary state 43 of a set of 8 processing queues as may be used by system 100. Exemplary state 43 may be similar to exemplary state 42 of FIG. 4B, except that some concurrent portions of individual messages have been processed (e.g., by portion processing component 114) in most processing queues. The status "C" may indicate the concurrent portion of a message has been processed (e.g., by some component of system 100), and the sequential portion of the particular message may be ready for processing, e.g. responsive to the particular message being the oldest message in the processing queue. The status of newly selected slots is "S", such as slot "a" of processing queue $Q_5$.

Subset determination component 116 may be configured to determine a subset of messages in a processing queue. For example, subset determination component 116 may be configured to determine a subset of messages in the third processing queue (e.g., as selected by processing queue selection component 110). In some implementations, determinations of subsets may be based on the messages in the subset being the oldest messages in the particular processing queue. In some implementations, the determination of being the oldest messages may be based on the timestamps reflecting the times of receipt of the messages in the third subset. In some implementations, the number of messages in a determined subset may be limited by a maximum number. In some implementations, the maximum number of messages in a subset may be 2, 4, 6, 8, 16, 32, and/or another number.

Numbering assignment component 118 may be configured to assign a numbering to a group of messages. For example, numbering assignment component 118 may be configured to assign a numbering the messages in a subset (e.g., as determined by subset determination component 116). In some implementations, a numbering may be sequential.

Numbering assignment component 118 may be configured to assign a second (sequential) numbering to those messages in the same subset that have a concurrent portion that has been previously processed and a sequential portion that has not been previously processed.

By way of non-limiting example, FIG. 4D illustrates (within a dashed line) an exemplary state 44 of a processing queue as may be used by system 100. Exemplary state 44 may be similar to the state of $Q_0$ in FIG. 4C. Subset determination component 116 may have determined a subset that includes the slots from "a" to "j," in other words 10 slots. Numbering assignment component 118 may have assigned a first sequential numbering 45 to the determined subset. First numbering 45 may range from number "0" to number "9". Numbering assignment component 118 may have assigned a second numbering 46 to those messages in the determined subset having status "C". Second numbering 46 may range from number "0" to number "6", and certain slots have been skipped because their status was not "C".

Referring to FIG. 1, message determination component 120 may be configured to determine an oldest message in a group of messages. For example, message determination component 120 may be configured to determine an oldest message in a subset (e.g., as determined by subset determination component 116). In some implementations, determinations by message determination component 120 may be based on the timestamps reflecting the times of receipt for the messages in the subset. In some implementations, message determination component 120 may be configured to determine multiple messages that are the oldest messages in a subset.

By way of non-limiting example, the oldest message in the processing queue depicted in FIG. 4D may be the message in the left-most slot. This may be slot "a".

Referring to FIG. 1, message determination component 120 may be configured to determine whether the oldest message in a subset was assigned the same number in different numberings (e.g., as assigned by numbering assignment component 118). For example, message determination component 120 may be configured to determine whether the oldest message in a subset was assigned the same number in the first sequential numbering and the second sequential numbering.

By way of non-limiting example, the oldest message in the processing queue depicted in FIG. 4D may have a first number of 0 from first numbering 45, and a second number 0 from second number 46. As depicted here, the assigned numbers are the same.

Referring to FIG. 1, portion processing component 114 may be configured to, responsive to a positive determination (e.g. by message determination component 120 regarding the assignment of the same number in different numberings), process the sequential portion of the oldest message. For example, the sequential portion of the oldest message in the processing queue depicted in FIG. 4D may be processed, such that both the concurrent and sequential portions are completed.

Message removing component 122 may be configured to remove messages from the set of processing queues. For example, message removing component 122 may be configured to remove the oldest message from the set of processing queues (in particular, after both the concurrent and sequential portions of the message have been processed). In some implementations, removal of a particular message may be responsive to a positive determination (e.g. by message determination component 120 regarding the assignment of the same number in different numberings), and/or responsive to processing of the sequential portion of the particular message.

For example, the sequential portions of the messages with numbers "0", "1", "2", "3", and "4" in the processing queue depicted in FIG. 4D may be processed (in order), because the assigned numbers for first numbering 45 and second numbering 46 are the same. Subsequently, both the concurrent and sequential portions for these messages are completed, and these messages may be removed from their processing queue. The assigned numbers for the remaining messages in this processing queue are not the same. As a result, the sequential portions of these messages may not yet be processed.

Message transmittal component 124 may be configured to transmit messages to one or more vendor entities. In some implementations, message transmittal component 124 may be configured to transmit one or more messages that have been completed processed to a particular vendor entity. In some implementations, message transmittal component 124 may be configured to transmit one or more messages that have been completed processed to multiple vendor entities. In some implementations, message transmittal component 124 may be configured to transmit a particular message to a particular vendor entity subsequent to processing of its sequential portion (since this implies the concurrent portions must have been previously processed). In some implementations, message transmittal component 124 may be configured to transmit the one or more oldest messages to a particular vendor entity. In some implementations, message transmittal component 124 may be configured to transmit messages to re-enter processing queues 129. For example, an individual message may need multiple passes to be processed. For example, message transmittal component 124 may be configured to copy and/or clone individual messages, modify the individual messages, and transmit the individual messages to re-enter processing queues 129. For example, a modification may include a change to identify a different destination.

In some implementations, server(s) 102, client computing platform(s) 104, and/or external resources 126 may be operatively linked via one or more electronic communication links. For example, such electronic communication links may be established, at least in part, via a network 13 such as the Internet and/or other networks. It will be appreciated that this is not intended to be limiting, and that the scope of this disclosure includes implementations in which server(s) 102, client computing platform(s) 104, and/or external resources 126 may be operatively linked via some other communication media.

A given client computing platform 104 may include one or more processors configured to execute computer program components. The computer program components may be configured to enable an expert or user associated with the given client computing platform 104 to interface with system 100 and/or external resources 126, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 126 may include sources of information outside of system 100, external entities participating with system 100, and/or other resources. In some implementations, some or all of the functionality attributed herein to external resources 126 may be provided by resources included in system 100. In some implementations, one or more healthcare entities may be regarded as part of external resources 126. In some implementations, one or more vendor entities may be regarded as part of external resources 126.

Server(s) 102 may include electronic storage 128, one or more processors 130, and/or other components. Server(s) 102 may include communication lines, or ports to enable the exchange of information with network 13 and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 128 may comprise non-transitory storage media that electronically stores information. The electronic storage media of electronic storage 128 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from server(s) 102, information received from client computing platform(s) 104, and/or other information that enables server(s) 102 to function as described herein.

Processor(s) 130 may be configured to provide information processing capabilities in server(s) 102. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 108, 110, 112, 114, 116, 118, 120, 122, and/or 124, and/or other components. Processor(s) 130 may be configured to execute components 108, 110, 112, 114, 116, 118, 120, 122, and/or 124, and/or other components by software; hardware; firmware; some combination of software, hardware, and/or firmware; and/or other mechanisms for configuring processing capabilities on processor(s) 130. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, 116, 118, 120, 122, and/or 124 are illustrated in FIG. 1 as being implemented within a single processing unit, in implementations in which processor(s) 130 includes multiple processing units, one or more of components 108, 110, 112, 114, 116, 118, 120, 122, and/or 124 may be implemented remotely from the other components. The description of the functionality provided by the different components 108, 110, 112, 114, 116, 118, 120, 122, and/or 124 described below is for illustrative purposes, and is not intended to be limiting, as any of components 108, 110, 112, 114, 116, 118, 120, 122, and/or 124 may provide more or less functionality than is described. For example, one or more of components 108, 110, 112, 114, 116, 118, 120, 122, and/or 124 may be eliminated, and some or all of its functionality may be provided by other ones of components 108, 110, 112, 114, 116, 118, 120, 122, and/or 124. As another example, processor(s) 130 may be configured to execute one or more additional components that may perform some or all of the functionality attributed below to one of components 108, 110, 112, 114, 116, 118, 120, 122, and/or 124.

Figure 2:
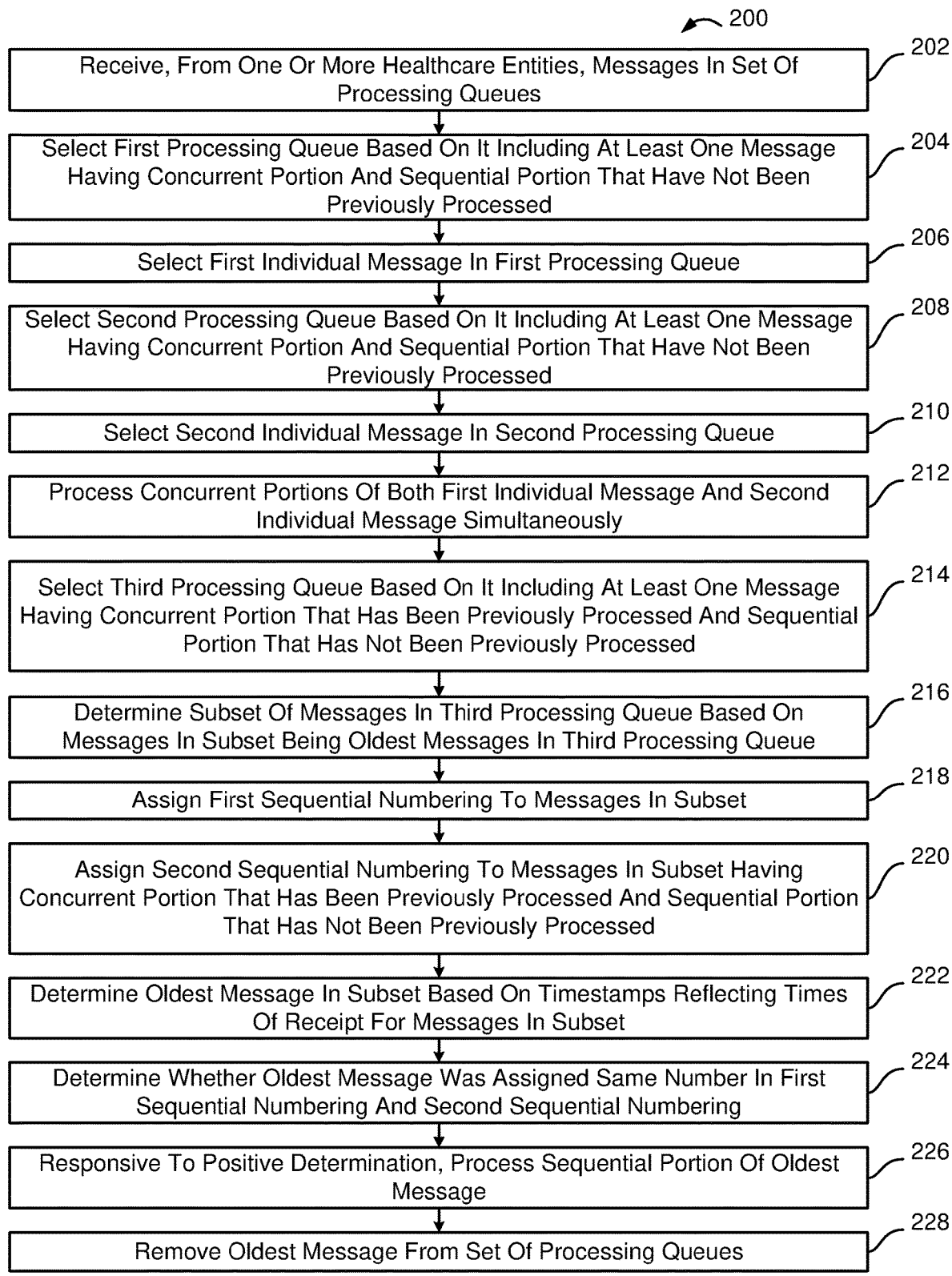
FIG. 2 includes a flow chart of a method to organize the flow and processing of queued messages, wherein the messages are received from healthcare entities, in accordance with one or more implementations.

FIG. 2 illustrates a method 200 to organize the flow and processing of queued messages, wherein the messages are received from healthcare entities, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include receiving, from one or more healthcare entities, messages in a set of processing queues. The set of processing queues may include more than two processing queues. Individual messages may be received in individual processing queues. The individual messages may include a timestamp reflecting a time of receipt, the individual messages further including a concurrent portion and/or a sequential portion. Operation 202 may be performed by one or more hardware processors configured by machine-readable instructions including a component that is the same as or similar to message receiving component 108, in accordance with one or more implementations.

An operation 204 may include selecting a first processing queue from the set of processing queues based on the first processing queue including at least one message having a concurrent portion and a sequential portion that have not been previously processed, e.g., by the set of processing queues. Operation 204 may be performed by one or more hardware processors configured by machine-readable instructions including a component that is the same as or similar to processing queue selection component 110, in accordance with one or more implementations.

An operation 206 may include selecting a first individual message in the first processing queue. Operation 206 may be performed by one or more hardware processors configured by machine-readable instructions including a component that is the same as or similar to message selection component 112, in accordance with one or more implementations.

An operation 208 may include selecting a second processing queue from the set of processing queues based on the second processing queue including at least one message having a concurrent portion and a sequential portion that have not been previously processed, e.g., by the set of processing queues. Operation 208 may be performed by one or more hardware processors configured by machine-readable instructions including a component that is the same as or similar to processing queue selection component 110, in accordance with one or more implementations.

An operation 210 may include selecting a second individual message in the second processing queue. Operation 210 may be performed by one or more hardware processors configured by machine-readable instructions including a component that is the same as or similar to message selection component 112, in accordance with one or more implementations.

An operation 212 may include processing the concurrent portions of both the first individual message and the second individual message simultaneously. Operation 212 may be performed by one or more hardware processors configured by machine-readable instructions including a component that is the same as or similar to portion processing component 114, in accordance with one or more implementations.

An operation 214 may include selecting a third processing queue from the set of processing queues based on the third selected processing queue including at least one message having a concurrent portion that has been previously processed and a sequential portion that has not been previously processed. Operation 214 may be performed by one or more hardware processors configured by machine-readable instructions including a component that is the same as or similar to processing queue selection component 110, in accordance with one or more implementations.

An operation 216 may include determining a subset of messages in the third processing queue based on the messages in the subset being the oldest messages in the third processing queue. The determination of being the oldest messages may be based on the timestamps reflecting the times of receipt of the messages in the third subset. Operation 216 may be performed by one or more hardware processors configured by machine-readable instructions including a component that is the same as or similar to subset determination component 116, in accordance with one or more implementations.

An operation 218 may include assigning a first sequential numbering to the messages in the subset. Operation 218 may be performed by one or more hardware processors configured by machine-readable instructions including a component that is the same as or similar to numbering assignment component 118, in accordance with one or more implementations.

An operation 220 may include assigning a second sequential numbering to the messages in the subset having a concurrent portion that has been previously processed and a sequential portion that has not been previously processed. Operation 220 may be performed by one or more hardware processors configured by machine-readable instructions including a component that is the same as or similar to numbering assignment component 118, in accordance with one or more implementations.

An operation 222 may include determining an oldest message in the subset based on the timestamps reflecting the times of receipt for the messages in the subset. Operation 222 may be performed by one or more hardware processors configured by machine-readable instructions including a component that is the same as or similar to message determination component 120, in accordance with one or more implementations.

An operation 224 may include determining whether the oldest message was assigned the same number in the first sequential numbering and the second sequential numbering. Operation 224 may be performed by one or more hardware processors configured by machine-readable instructions including a component that is the same as or similar to message determination component 120, in accordance with one or more implementations.

An operation 226 may include responsive to a positive determination, processing the sequential portion of the oldest message. Operation 226 may be performed by one or more hardware processors configured by machine-readable instructions including a component that is the same as or similar to portion processing component 114, in accordance with one or more implementations.

An operation 228 may include removing the oldest message from the set of processing queues. Operation 228 may be performed by one or more hardware processors configured by machine-readable instructions including a component that is the same as or similar to message removing component 122, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to organize flow and processing of queued messages, wherein the messages are received from healthcare entities, the system comprising:
    one or more hardware processors configured by machine-readable instructions to:
        receive, from the healthcare entities, the messages in a set of processing queues, wherein the set of processing queues includes more than two processing queues, wherein individual ones of the messages are received in individual ones of the processing queues in the set of processing queues, wherein the individual ones of the messages include individual timestamps reflecting time of receipt, the individual ones of the messages further including a concurrent portion and/or a sequential portion;
        select a first processing queue from the set of processing queues based on the first processing queue including at least one message having the concurrent portion and the sequential portion that have not been previously processed by the set of processing queues and a set of processing engines;
        select a first individual message in the first processing queue, the first individual messaging having a first concurrent portion and a first sequential portion;
        select a second processing queue from the set of processing queues based on the second processing queue including at least one message having the concurrent portion and the sequential portion that have not been previously processed by the set of processing queues and the set of processing engines;
        select a second individual message in the second processing queue, the second individual messaging having a second concurrent portion and a second sequential portion;
        process both of the first concurrent portion of the first individual message and the second concurrent portion of the second individual message simultaneously;
        select a third processing queue from the set of processing queues based on the third selected processing queue including at least one message having the concurrent portion that has been previously processed by the set of processing queues and the set of processing engines, and the sequential portion that has not been previously processed by the set of processing queues and the set of processing engines;
        determine a subset of the messages in the third processing queue based on the messages in the subset being oldest messages in the third processing queue, wherein the determination of being the oldest messages is based on the individual timestamps reflecting the time of receipt of the messages in the third processing queue;
        assign a first sequential numbering to the messages in the subset;
        assign a second sequential numbering to the messages in the subset having (i) a given concurrent portion that has been previously processed, and (ii) a given sequential portion that has not been previously processed;
        determine an oldest message in the subset based on the individual timestamps reflecting the time of receipt for the messages in the subset;
        determine whether the oldest message was assigned a same number in the first sequential numbering and the second sequential numbering;
        responsive to a positive determination, process the sequential portion of the oldest message; and
        remove the oldest message from the set of processing queues.

2. The system of claim 1, wherein the individual ones of the processing queues are assigned to individual ones of the healthcare entities, and wherein the individual ones of the messages represent events involving subjects and assets of the individual ones of the healthcare entities.

3. The system of claim 2, wherein the individual ones of the messages each have a format that is specific to one or more of the healthcare entities.

4. The system of claim 1, wherein processing both of the first concurrent portion of the first individual message and the second concurrent portion of the second individual message simultaneously includes processing at least a first segment of the first concurrent portion of the first individual message at a same time as processing at least a second segment of the second concurrent portion of the second individual message.

5. The system of claim 1, wherein the sequential portion of the individual ones of the messages needs to be processed after the concurrent portion of the individual ones of the messages.

6. The system of claim 1, wherein processing of the concurrent portion of the individual ones of the messages is performed by one or more processing engines from the set of processing engines.

7. The system of claim 6, wherein selecting the first individual message in the first processing queue includes rendering the first individual message unavailable for selection by other ones of the processing engines in the set of processing engines.

8. The system of claim 1, wherein processing of the concurrent portion of the individual ones of the messages includes transforming contents and/or formatting of the concurrent portion of the individual ones of the messages.

9. The system of claim 8, wherein processing of the concurrent portion of the individual ones of the messages includes transforming the formatting of the concurrent portion of the individual ones of the messages, wherein transforming the formatting of the concurrent portion of the individual ones of the messages causes the individual ones of the messages to have a format that is common among two or more of the healthcare entities.

10. The system of claim 1, wherein the one or more hardware processors are further configured by the machine-readable instructions to:
transmit the oldest message to a particular vendor entity.

11. A method to organize flow and processing of queued messages, wherein the messages are received from healthcare entities, the method comprising:
receiving, from the healthcare entities, the messages in a set of processing queues, wherein the set of processing queues includes more than two processing queues, wherein individual ones of the messages are received in individual ones of the processing queues in the set of processing queues, wherein the individual ones of the messages include individual timestamps reflecting time of receipt, the individual ones of the messages further including a concurrent portion and/or a sequential portion;
selecting a first processing queue from the set of processing queues based on the first processing queue including at least one message having the concurrent portion and the sequential portion that have not been previously processed by the set of processing queues and a set of processing engines;
selecting a first individual message in the first processing queue, the first individual messaging having a first concurrent portion and a first sequential portion;
selecting a second processing queue from the set of processing queues based on the second processing queue including at least one message having the concurrent portion and the sequential portion that have not been previously processed by the set of processing queues and the set of processing engines;
selecting a second individual message in the second processing queue, the second individual messaging having a second concurrent portion and a second sequential portion;
processing both of the first concurrent portion of the first individual message and the second concurrent portion of the second individual message simultaneously;
selecting a third processing queue from the set of processing queues based on the third selected processing queue including at least one message having the concurrent portion that has been previously processed by the set of processing queues and the set of processing engines, and the sequential portion that has not been previously processed by the set of processing queues and the set of processing engines;
determining a subset of the messages in the third processing queue based on the messages in the subset being oldest messages in the third processing queue, wherein the determination of being the oldest messages is based on the individual timestamps reflecting the time of receipt of the messages in the third processing queue;
assigning a first sequential numbering to the messages in the subset,
assigning a second sequential numbering to the messages in the subset having (i) a given concurrent portion that has been previously processed, and (ii) a given sequential portion that has not been previously processed;
determining an oldest message in the subset based on the individual timestamps reflecting the time of receipt for the messages in the subset;
determining whether the oldest message was assigned a same number in the first sequential numbering and the second sequential numbering;
responsive to a positive determination, processing the sequential portion of the oldest message; and
removing the oldest message from the set of processing queues.

12. The method of claim 11, wherein the individual ones of the processing queues are assigned to individual ones of the healthcare entities, and wherein the individual messages represent events involving subjects and assets of the individual ones of the healthcare entities.

13. The method of claim 12, wherein the individual ones of the messages each have a format that is specific to one or more of the healthcare entities.

14. The method of claim 11, wherein processing both of the first concurrent portion of the first individual message and the second concurrent portion of the second individual message simultaneously includes processing at least a first segment of the first concurrent portion of the first individual message at a same time as processing at least a second segment of the second concurrent portion of the second individual message.

15. The method of claim 11, wherein the sequential portion of the individual ones of the messages needs to be processed after the concurrent portion of the individual ones of the messages.

16. The method of claim 11, wherein processing of the concurrent portion of the individual ones of the messages is performed by one or more processing engines from the set of processing engines.

17. The method of claim 16, wherein selecting the first individual message in the first processing queue includes rendering the first individual message unavailable for selection by other ones of the processing engines in the set of processing engines.

18. The method of claim 11, wherein processing of the concurrent portion of the individual ones of the messages includes transforming contents and/or formatting of the concurrent portion of the individual ones of the messages.

19. The method of claim 18, wherein processing of the concurrent portion of the individual ones of the messages includes transforming the formatting of the concurrent portion of the individual ones of the messages, wherein transforming the formatting of the concurrent portion of the individual ones of the messages causes the individual ones of the messages to have a format that is common among two or more of the healthcare entities.

20. The method of claim 11, further comprising:
transmitting the oldest message to a particular vendor entity.

* * * * *

UNITED STATES PATENT AND TRADEMARK OFFICE
CERTIFICATE OF CORRECTION

PATENT NO. : 10,937,553 B2
APPLICATION NO. : 16/189609
DATED : March 2, 2021
INVENTOR(S) : Blake Rego et al.

Page 1 of 1

It is certified that error appears in the above-identified patent and that said Letters Patent is hereby corrected as shown below:

In the Claims

Claim 1, Column 18, Line 2, delete "messaging" and insert --message--, therefor.

Claim 1, Column 18, Line 11, delete "messaging" and insert --message--, therefor.

Claim 11, Column 19, Line 50, delete "messaging" and insert --message--, therefor.

Claim 11, Column 19, Lines 59, delete "messaging" and insert --message--, therefor.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*